(12) United States Patent
Lechot et al.

(10) Patent No.: US 8,491,586 B2
(45) Date of Patent: Jul. 23, 2013

(54) HOLDER FOR A SURGICAL REAMER AND SINGLE USE, FLAT REAMER

(75) Inventors: André Lechot, Orvin (CH); Yann Rossé, Préles (CH); Didier Guélat, Porrentruy (CH)

(73) Assignee: Greatbatch Medical S.A., Orvin (CH)

( * ) Notice: Subject to any disclaimer, the term of this patent is extended or adjusted under 35 U.S.C. 154(b) by 1500 days.

(21) Appl. No.: 12/026,564

(22) Filed: Feb. 6, 2008

(65) Prior Publication Data
US 2008/0195101 A1 Aug. 14, 2008

Related U.S. Application Data

(60) Provisional application No. 60/888,880, filed on Feb. 8, 2007.

(51) Int. Cl.
*A61B 17/56* (2006.01)
*A61B 17/32* (2006.01)
*A61B 19/02* (2006.01)

(52) U.S. Cl.
USPC .................. 606/81; 606/79; 606/80; 606/85; 606/167; 606/171; 606/180

(58) Field of Classification Search
USPC ............... 606/79–85, 167, 171, 180; 279/93, 279/94; 408/204
See application file for complete search history.

(56) References Cited

U.S. PATENT DOCUMENTS

| 4,621,637 A | 11/1986 | Fishbein |
| 5,171,313 A | 12/1992 | Salyer |
| 5,236,433 A | 8/1993 | Salyer |
| 5,282,804 A | 2/1994 | Salyer |
| 5,295,992 A | 3/1994 | Cameron |
| 5,376,092 A | 12/1994 | Hein et al. |
| 5,501,686 A | 3/1996 | Salyer |
| 5,658,290 A | 8/1997 | Lechot |
| 5,976,144 A | 11/1999 | Fishbein et al. |
| 6,221,076 B1 | 4/2001 | Albrektsson et al. |
| 6,264,647 B1 | 7/2001 | Lechot |
| 6,277,121 B1 * | 8/2001 | Burkinshaw et al. ........... 606/80 |
| 6,475,221 B1 * | 11/2002 | White et al. .................... 606/80 |
| 6,783,532 B2 | 8/2004 | Steiner et al. |

(Continued)

FOREIGN PATENT DOCUMENTS
EP 0704191 4/1996
WO WO00/13595 3/2000

(Continued)

*Primary Examiner* — Kevin T Truong
*Assistant Examiner* — Tracy Kamikawa
(74) *Attorney, Agent, or Firm* — Michael F. Scalise (57) ABSTRACT

Disclosed is a surgical tool holder adapted to connect to a disposable cutting tool, and the surgical instrument combination. The tool holder has a shank with a quick tool coupling at one end and a drive adaptor at a second end. The coupling assembly has a coupling interface for holding the tool, and has a debris reservoir. A locking mechanism is engageable with the shank by a lock interface that holds the coupling assembly in functional assembly, and when unlocked allows component parts of the coupling assembly to be separated for cleaning and sterilization. The surgical tool has a flat base and complementary fittings adapted to be received by the holder's coupling interface. The combination of the flat base with the reservoir defines a relatively enclosed collection space to receive cutting debris from the tool while the holder and tool are coupled together.

28 Claims, 8 Drawing Sheets

U.S. PATENT DOCUMENTS

| | | |
|---|---|---|
| 6,783,533 B2 | 8/2004 | Green et al. |
| 6,854,742 B2 * | 2/2005 | Salyer et al. ............. 606/80 |
| 6,890,336 B2 * | 5/2005 | Nordman ............. 606/80 |
| 6,951,562 B2 * | 10/2005 | Zwirnmann ............. 606/80 |
| 7,074,224 B2 | 7/2006 | Daniels et al. |
| 7,220,264 B1 | 5/2007 | Hershberger |
| 7,278,996 B2 | 10/2007 | Wolford |
| 2005/0085821 A1 | 4/2005 | Wolford |
| 2005/0124981 A1 * | 6/2005 | Desarzens et al. ............. 606/1 |
| 2006/0100631 A1 | 5/2006 | Sullivan et al. |
| 2008/0021478 A1 | 1/2008 | Wolford |

FOREIGN PATENT DOCUMENTS

| | | |
|---|---|---|
| WO | WO2004/098421 | 11/2004 |
| WO | WO2004/100805 | 11/2004 |
| WO | 2006062762 | 6/2006 |

* cited by examiner

HOLDER FOR A SURGICAL REAMER AND SINGLE USE, FLAT REAMER

CROSS-REFERENCE TO RELATED APPLICATIONS

The present application claims the benefit of prior filed U.S. Provisional application Ser. No. 60/888,880, filed 8 Feb. 2007, and U.S. application Ser. No. 11/962,562 filed 21 Dec. 2007, which applications are fully incorporated herein by reference.

FIELD OF THE INVENTION

The present invention is in the field of orthopedic surgical instrumentation for use in operative surgery on a bone structure in the body (believed to be: class/subclass: 606/1; 53). Specifically, the present invention relates to surgical instrumentation means to assist in the removal, repair or replacement of bone tissue (believed to be: subclass: 86), and wherein significance is attributed to a cutting means particularly adapted to cut into bone and/or associated softer bone-like tissues of the body (believed to be: subclass: 79).

BACKGROUND OF THE INVENTION

The present invention relates to surgical instrument holders, and more particularly, to hand-held holders of rotary orthopedic bone cutting tools. Surgical instruments and their respective holders have to be kept clean and sterile before any use in a hospital environment in order to minimize risk of transfer of disease or infection from patient to patient following the emergence of certain "prions" that are not killed by normal hospital sterilization and thus need to be physically removed through washing and rinsing. A surgical instrument, for example for preparing for the fitting of a hip prosthesis, works in a medium which causes considerable soiling of both the instrument and the instrument holder. Despite the importance of doing so, the thorough cleaning of these devices is difficult. Surgical instrument holders of the prior art are designed such that washing and rinsing are generally not an effective way of cleaning the instrument. This is due to the small spaces left between component parts which allow only minimal access by cleaning agents.

It is desirable to collect bone fragments as a reamer cuts. Reamers typically have a concave or convex structural portion which can provide an integrated space in which bone fragments may be collected during cutting. However, this requires the reamer to have a complex, 3-dimensional configuration, the reamer being concave or convex in some respect. An integral collection space in a reamer having a complex configuration can make cleaning and sterilization difficult, and can require relatively exceptional attention to accomplish. Additionally, the reamer is typically just the tool head portion of a reamer tool and a tool handle/holder combination. The tool head and tool holder can be integrally combined, or the tool head can be detachable from the tool holder. The holder must also be cleaned and sterilized between uses.

It is advantageous to the field that surgical instruments be available that can easily be brought to the appropriate level of cleanliness and sterility, or that are configured to avoid potential cleanliness and sterility problems. To promote improved levels of cleanliness and sterility, those active in the field have been motivated to develop "single use" or disposable surgical instrument and instrument components. However, single use surgical instrument and/or their component parts should be simple in order to make them inexpensive enough that discarding them makes economical sense. The current benefit in the field of orthopedic surgical reamers having a built-in (integral) debris collection space for holding bone tissue fragments does not generally admit of simple reamer tool configurations.

It would be beneficial to the orthopedic surgical instruments field to have available a reamer tool and a tool handle/holder combination for which appropriate cleanliness and sterility after use can be easily accomplished. What is needed is a separable reamer tool and tool holder combination which is simple, relatively inexpensive to manufacture and at least in part disposable. Still further, what is needed is a tool holder that is easily and quickly disassemblable for cleaning and sterilization.

SUMMARY OF THE INVENTION

The present invention is a combination, orthopedic surgical instrument comprising combination of a surgical tool holder and a surgical tool head. The tool has a base portion that, when the tool holder and the tool head are assembled, cooperate to provide the combination instrument with an enclosed debris collection space that does not exist in the separate components. Because the enclosed collection space does not exist outside of the combination, cleaning and sterilization of the instrument is greatly facilitated. The surgical instrument holder of the present invention has a shank having a first drivable end and a second coupling end, a coupling device mounted on the coupling end, and a locking mechanism. The coupling end has an interface thereon for receiving an instrument. The locking mechanism in made up of an annular locking component, a spring, a ring which slides on the shank, and a locking device. The annular locking component is mounted so as to slide along the shank. The locking device cooperates with the locking component so as to lock the instrument onto the interface. The spring biases the locking component in a locking direction and bears on the ring. The ring is reversibly lockable to the shank via a connection device.

An object of the invention is to provide a combination tool head/tool holder orthopedic instrument having an "enclosed" cutting debris collection space that does not require the disposable tool itself to be formed of a complex shape. It is additionally an object that the separate holder can be easily and quickly disassemble for cleaning and component sterilization. A further object is to provide such combination having a disposable reamer/cutter tool head that is simply configured, relatively inexpensive to manufacture and easily attachable to the holder.

DETAILED DESCRIPTION OF THE INVENTION

Referring now to the drawings, the details of preferred embodiments of the present invention are graphically and schematically illustrated. Like elements in the drawings are represented by like numbers, and any similar elements are represented by like numbers with a different lower case letter suffix.

Figure 6:
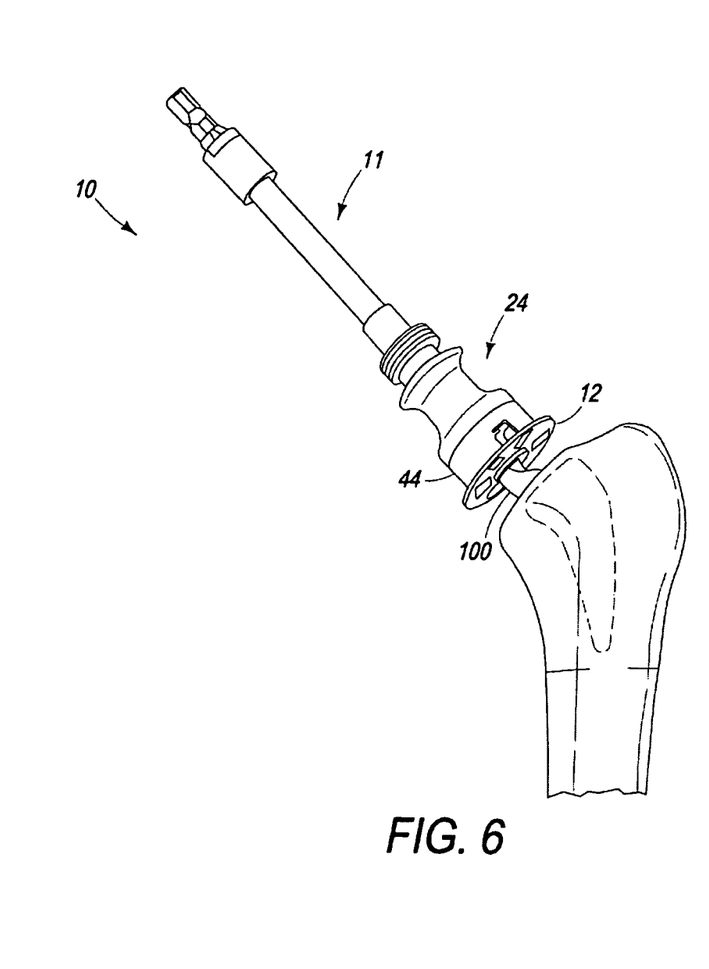
FIG. 6 is a perspective view of the present instrument combination showing a rasp/reamer tool head attached to the holder and the combination instrument receiving the stem of another tool disposed at a bone work site.

The present invention is a combination orthopedic surgical instrument 10 useful in situ for forming bone surfaces (see FIG. 6). The instrument 10 comprises a surgical tool holder 11 combinable with a surgical tool head 12 (or simply: the tool 12). The holder 11 has a quick coupling assembly 24 for attaching the holder 11 to the tool 12. The "quick" feature of the coupling assembly 24 resides in its ability to receive and lock onto a tool 12 simply by pressing the tool 12 onto the tool interface of the assembly 24 and rotating the tool 12 a small angle A to cause the assembly to automatically secure the tool 12 to the holder 11. The coupling assembly 24 includes an "open" debris reservoir 40. The tool 12 adapted to interface with reservoir 40 of the coupling assembly 24. The tool 12 has a flat base portion 104 that, when the tool holder 11 and the tool 12 are assembled, cooperate with the open debris reservoir 40 to provide the combination instrument 10 with an enclosed debris collection space that the separated components do not have.

Figure 1A:
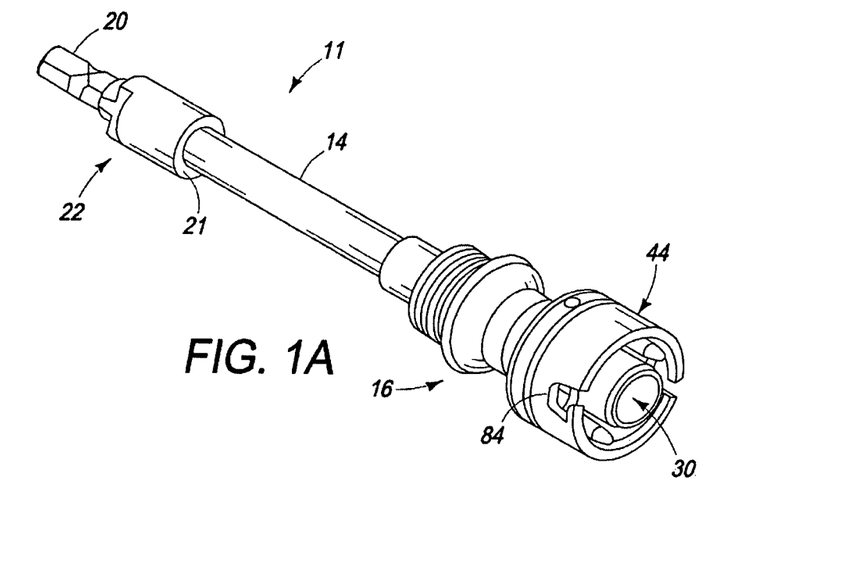
FIGS. 1A and 1B are perspective views of a first embodiment of the instrument holder of the invention with the locking mechanism in a normally locked condition (A), and in an unlocked condition with the coupling assembly components separated along the shaft to provide cleaning access to the components and full sterilization access (B).
Figure 1B:
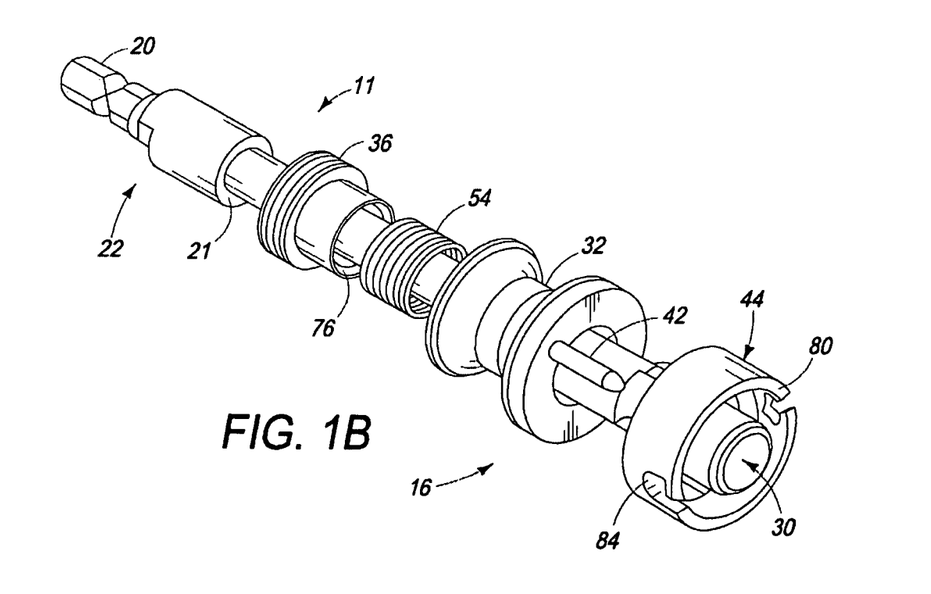
Figure 1C:
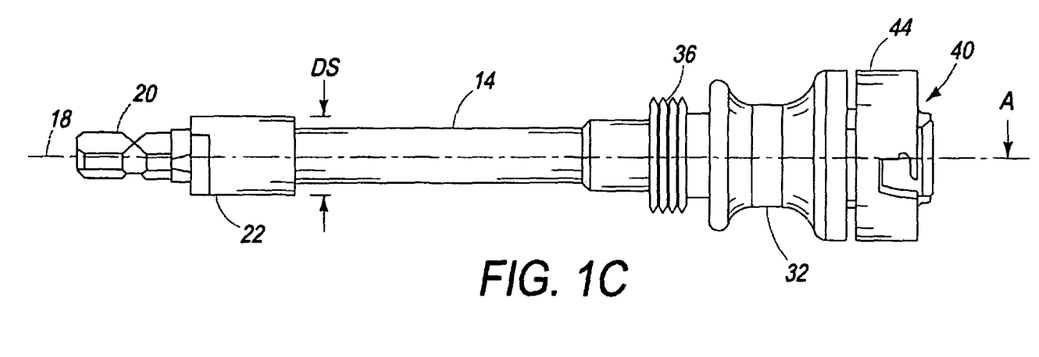
FIGS. 1C and 1D are side views of the embodiment of the instrument holder of the FIGS. 1A and 1B, with the locking mechanism in a normally locked condition (C), and in an unlocked condition with the coupling assembly components separated along the shaft to provide access to the components for cleaning and full sterilization (D).
Figure 1D:
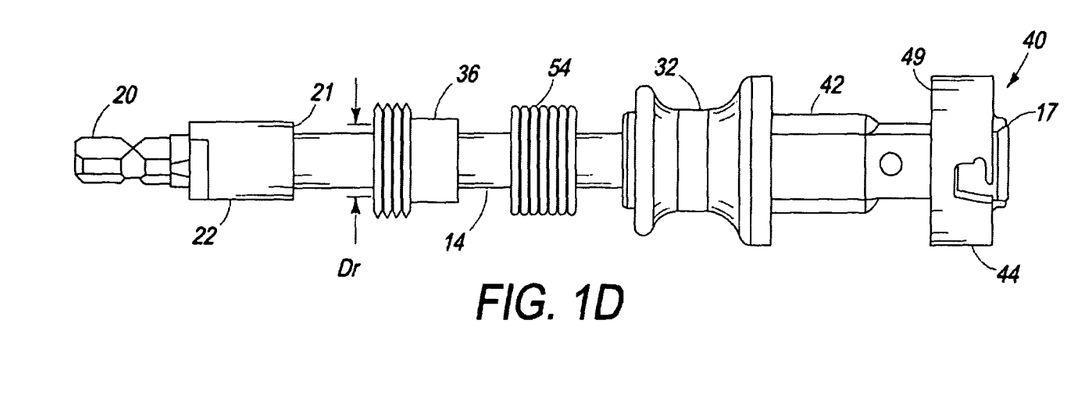
Figures 2A, 2B:
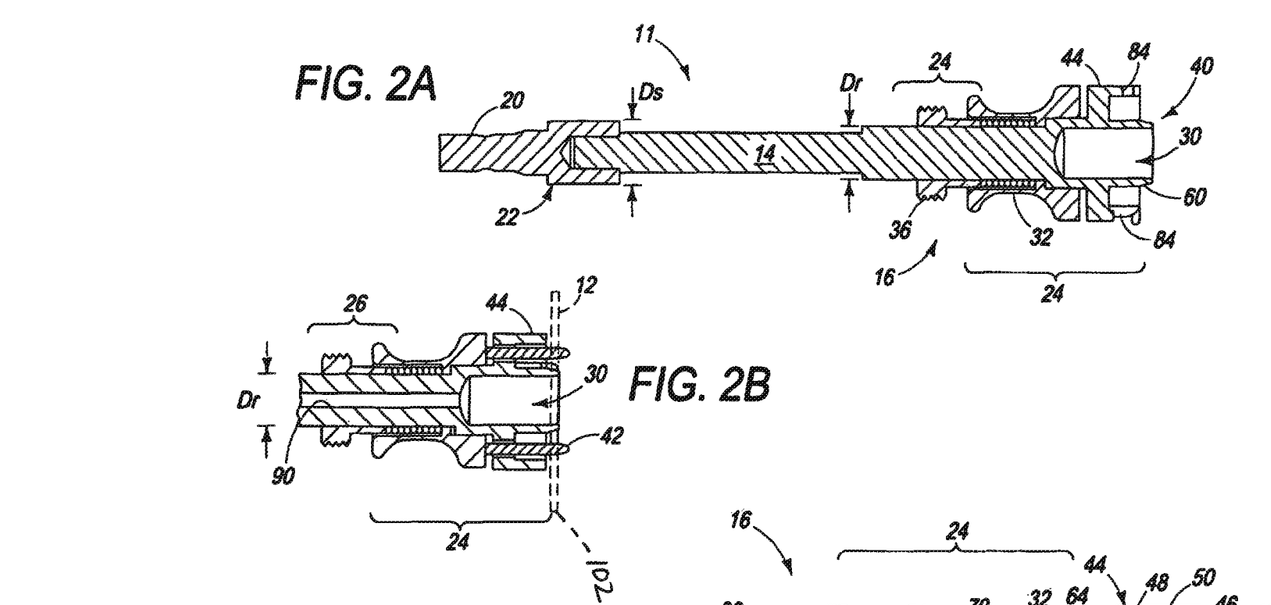
FIGS. 2A and 2B respectively are cross-sectional views of the holder through the fitting slots (J-slots) of plane "A" of FIG. 1C, and through the detent pins.

FIGS. 1A-1D illustrate an embodiment of the tool holder 11 of the present invention. The holder 11 connects to a surgical tool 12 to enable controlled manipulation of the tool 12. Preferably, the tool 12 is flat and "void-less." "Void-less" means that the tool 12 has no integrally defined enclosed or relatively enclosed debris collecting space/chamber. The holder 11 has a shank portion 14, which substantially is an elongated, rod-like cylinder having a distal (from the user) coupling end 16 portion, a drive end 22 portion, and a central axis 18. As shown in FIG. 2A, proximate the coupling end 16, a quick coupling assembly 24 and a locking mechanism 26 are disposed. A driver/handle adaptor 20 is disposed at the opposite drive end 22 of the shank. The driver adaptor 20 allows the holder to be attached to a manipulator of some kind, such as a T-handle or other rotation means (not shown). The driver adaptor 20 in the embodiments illustrated is a typical male hex interface of a standard-type socket connect assembly, such as is know to the ordinary skilled artisan. Other types of connect interfaces are known to and selectable by the skilled artisan for practice as the adaptor 20 in the present invention, such as a standard-type female hex socket interface, a bayonet-type interface and either a large AO fitting or a small AO fitting. AO is a term known to one of ordinary skill in the field of orthopedic surgical devices. Specifically, as used herein, AO fitting refers to the widely used designation of a tool fitting standardized by the AO Institute of Colorado (founded by Synthes A. G. of Chur, Switzerland). An example of the use and understanding of the term in the field is evidenced by the following literature cite: Gholamhossein Kazemian, Saeed Kokly, Dariush Adybeik: *Bone Transport In Chronic Infected Non-Union Using AO External Fixator*, The Internet Journal of Orthopedic Surgery. 2004. Volume 2 Number 1.

Figure 7:
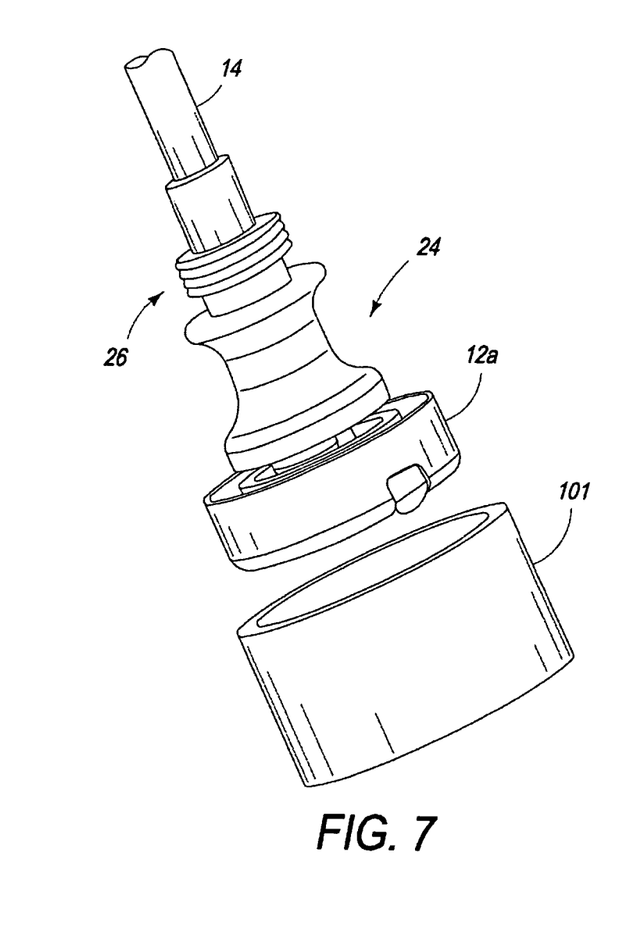
FIG. 7 is a perspective view of the coupling assembly at the shank end of the combination instrument engaged with a patella cutting tool head, wherein the tool head is positioned to be received by a cylindrical guide.

The coupling end 16 terminates in a guide portion 28 which at its distal end 17 has an internal guide recess 30 set into it for receiving a guide or alignment post 100. The guide recess 30 is coaxial with the central axis 18 of the shank 14. The surface of the recess 30 can serve as a bearing or bushing against which the guide post may slide and/or rotate. Optionally, the internal guide recess 30 is continuous with a cannula 90 (hollow bore) within the shank 14 and running internally along the axis 18 of the shank 14. The cannula 90 is in flow communication with the guide recess 30. The recess guide 30 in turn is in flow communication with the collection space 46 via one or more flow ports 52 (see FIG. 2E). The optional cannula 90 is useful for such purposes as lavage and to provide a channel for removing cutting debris from the collection space 46 of a reservoir 44 at the end of the coupling assembly 24. As shown in FIGS. 2A to 2D, the coupling end 16 is adapted to mount the reservoir structure 44, within the interior of which the guide portion 28 is disposed. The reservoir structure 44 surrounds the guide portion 28 and defines a collection space 46 between them. Additionally, the tool 12a may utilize a cylindrical guide 101 (see FIG. 7), preferably in combination with a guide post 100.

Figure 2C:
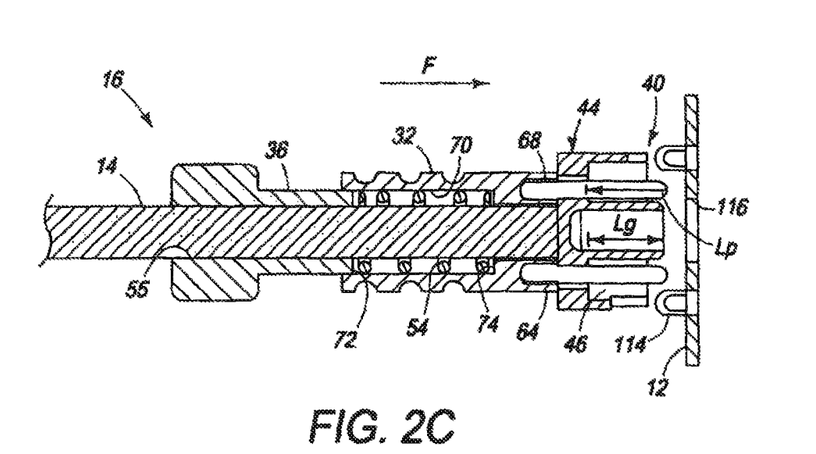
FIGS. 2C and 2D are partial cross-sectional views of an alternative embodiment of FIG. 2B, and respectively show the coupling assembly in a normal condition and the tool head position to be attached; and the coupling assembly forced into a retracted condition by the tool head being initially positioned on the holder, but not yet rotated and hence engaged by the holder.
Figure 2D:
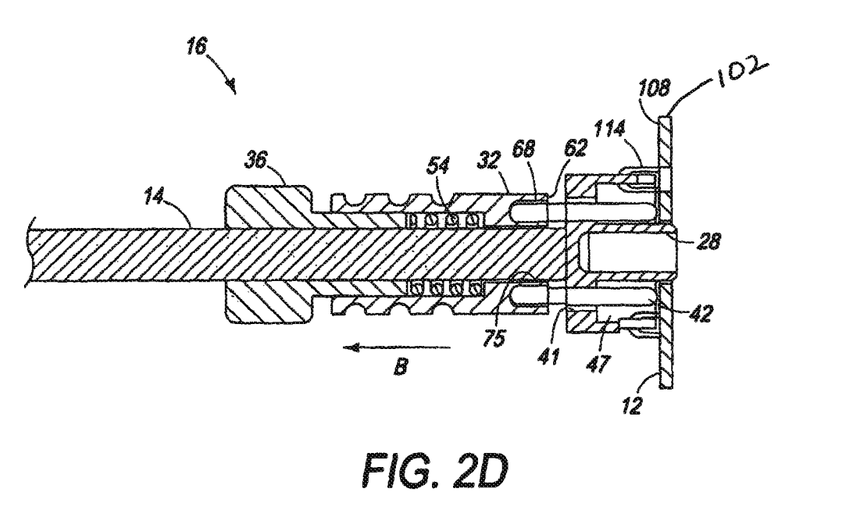

As shown in FIGS. 2C and 2D, the coupling mechanism comprises a collar/sleeve 32 and a bias member 54, which are slidably received about the shaft 14 proximate the coupling end 16. The collar 32 has a collar bore 60 through which the shank 14 slidably passes. The collar 32 has a collar face 62 disposed on a first collar end $4. At least one engagement pin 42 (and preferably two) projects from the collar face 62 parallel to the shank axis 18. In the embodiment illustrated, two engagement pins 42 were fixed in pin receptacles 68 set into the collar face 62 of the collar 32. The collar 32 has an internal chamber 70 open to a second collar end 72. The internal collar chamber 70 has a bottom seat 74 which interfaces with the bias member 54.

The biasing member 54 is slidably disposed around the shank 14 between the collar 32 and the locking ring 36. The biasing member 54 is receivable into the internal chamber 70 of the collar 32. A first bias end of the bias member is received against the bottom seat 74 of the collar 32. The second bias end of the biasing member 54 is received against the bias face 76 of the collar 56. In the illustrated embodiment, the bias face 76 of the collar 56 is receivable into the internal chamber 70 of the collar 32. In the embodiment illustrated in the figures, the biasing member 54 was a single helix coil spring. However, alternative biasing members are known to and selectable by one of ordinary skill in this field for practice in the present system 10. For example, a double helix coil spring or other elastic member could be used, so long as it can be appropriately cleaned and sterilized.

The biasing member 54, when set against a fixed bias interface 76 of the locking ring 36, applies a force against the coupling collar 32 biasing it in a forward direction F toward the coupling end 17. At least one coupling pin 42, and in the preferred embodiments two, project from the forward face 62 of the coupling collar 32 in a direction parallel to the axis 18 of the shank 14. The coupling pins 42 are normally biased to pass through a pin guide hole 41 in a base portion 48 of the reservoir 44, and to normally extend beyond the base portion 48 to a certain pin length Lp. The reservoir structure 44 has a base portion 48 with a stop surface 49 against which the forward face 62 of the coupling collar 32 normally bears. Side walls 50 extend a wall height H from the base portion 48, the base portion 48 and side walls 50 defining the collection space 46 of the reservoir 44, as being the space within the base portion 48 and side walls 50. The wall height H is slightly less than the pin length Lp as illustrated in the figures.

The terminal end 17 of the holder shank 14 terminates in a guide portion 28 having a guide recess 30 set within it. The guide portion 28 extends in a forward direction from the reservoir base portion 48 a distance of a guide length Lg. The guide length Lg is slight greater than the height H as illustrated in the figures. The side wall 50 of the reservoir 44 has a forward rim 80. The forward rim 80 has fitting slots 84 set into it. The fitting slots 84 are adapted to releasable engage a complementary fitting interface 112 on a tool 12. The forward rim 80 and the fitting slots 84 in combination with a front part 60 of the guide portion 28 define the tool interface of the coupling assembly 24. After the complementary fitting interface 114 of the tool 12 is received in the fitting slots of the reservoir wall 44, the tool 12 is rotated relative to the fitting slots 84 to engage the slots 84 with the complementary fitting interface 114 on the tool 12. The direction of the rotation is through an angle A, upon which rotation the fitting slots 84 engage fitting interfaces 114 on the tool 12 and the coupling pin 42 are caused to snap into their respective detents 112 on the tool 12.

Figure 2E:
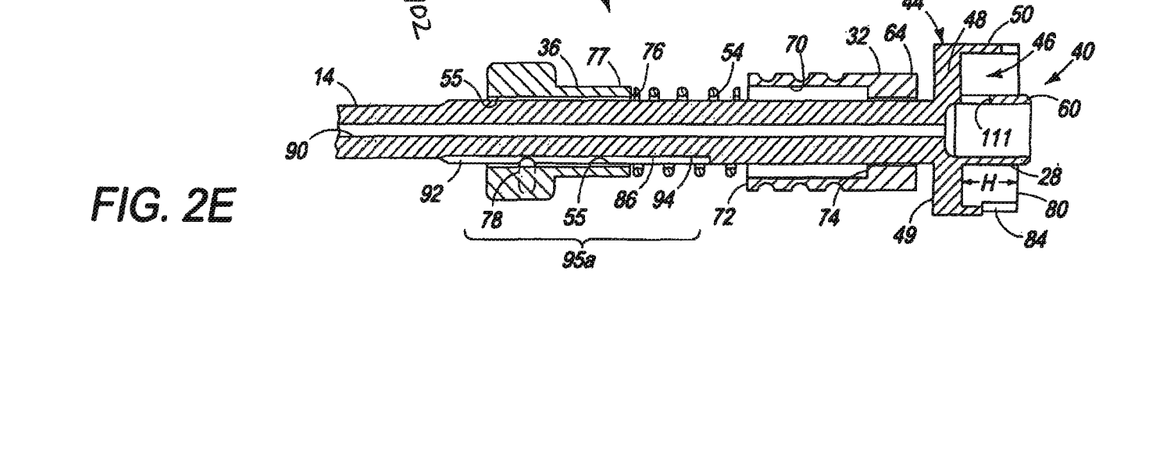
FIG. 2E is a cross-sectional view of the coupling end of the holder showing a bayonet-type locking mechanism in the unlocked condition and the components of the coupling assembly and locking mechanism disbursed along the length of the shank for cleaning and sterilization.

The locking mechanism 26, when locked, holds the components of the quick coupling mechanism 24 in an assembled condition. As illustrated in FIG. 2E, when the locking mechanism 26 is unlocked, the component parts of the quick coupling assembly 24 can be slid along the shank 14 of the holder 11 and separated from each other for easy cleaning and full sterilization. Further, the coupling assembly components are retained on the shank 14 by the stop face 21 on the drive adaptor 20. The locking mechanism 24 has an annular locking ring 36 that receives and is slidably along the shank 14. The annular locking ring 36 has an inner ring surface 55 with an inner ring diameter Dr. The drive end 22 has a stop shoulder 21 having a stop diameter Ds that is larger than the inner ring diameter Dr of the locking ring 20 to prevent the locking ring 20 from sliding off of the shank 14 when the lock interface 95a is unlocked.

The locking ring 36 is engageable with the shank 14 by a lock interface 95a (see FIG. 2E) that fixes the position of the ring on the shank 14 relative to the quick coupling assembly 24. When the locking ring 36 is engaged with the shank 14, the ring-bias interface 76 of the locking ring 36 provides a fixed (immovable) base against which the biasing means 54 of the quick coupling assembly 24 is set. This holds the coupling assembly 24 in functional assembly, and when unlocked allows component parts of the coupling assembly 24 to be easily separated for cleaning and sterilization. The lock interface 95a can be accomplished by any of a number of means known to the ordinary skilled artisan. In the embodiment shown in FIG. 3E, the lock interface 95a of the locking mechanism 26 is a set screw 38 tightened against the shank 14 or screwed into a detent (not shown) is used to fix the relative position of the annular ring 36 on the shank 14.

Other lock interface means 95a are known to and selectable by one of skill in the art for practice in the present invention. For example, FIG. 2E illustrates a bayonet-type lock interface 95a practicable in the present invention. As shown in FIG. 2E, the holder shank 14 has a tracking groove 86 inset into its surface. The tracking groove 86 runs parallel to the axis 18 of the shank 14 from a first groove end 88 to a second groove end 92 toward the adaptor end 22 of the shank 14. The tracking groove 86 has a release slot 94 disposed approximate the first groove end 88, the release slot 94 having an "L/J-like" configuration. The release slot 94 communicates with the tracking groove 86 and is a component of the lock interface 95a of the locking mechanism 26. A bayonet/guide pin 78 travels in the groove 86 and the slot 94. The release fitting 95a comprises a combination of the guide pin 78 and release slot 94 and tracking slot 86. In the preferred embodiment the release slot, was configured as a single "J"-slot, but could be a double J-slot, a "T"-slot or the like. The guide pin 78 radially projects from the inner ring surface 55 of the locking ring 36. The locking ring is manually operable to move the guide pin 78 along the tracking groove 86 and reversibly set it into the release slot against the force of the bias 54. When so set, the bias force locks the guide pin 78 in the release slot 94 and prevents inadvertent release of the locking mechanism 26.

Figure 4A:
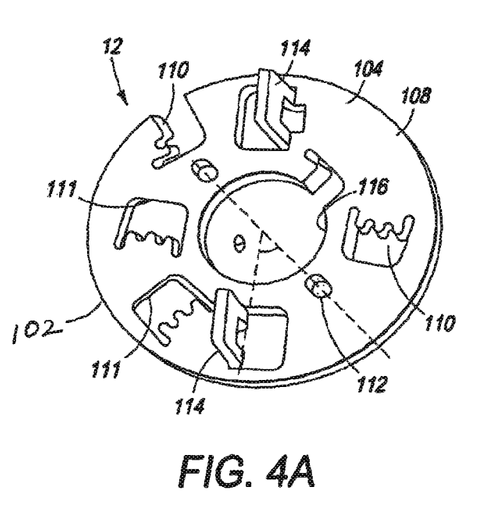
FIG. 4A is a perspective view of an embodiment of a single use, flat reamer/planer rasp tool head of the present combination instrument, showing structural details of the "back" (non-cutting) or mounting surface of the tool head.
Figure 4B:
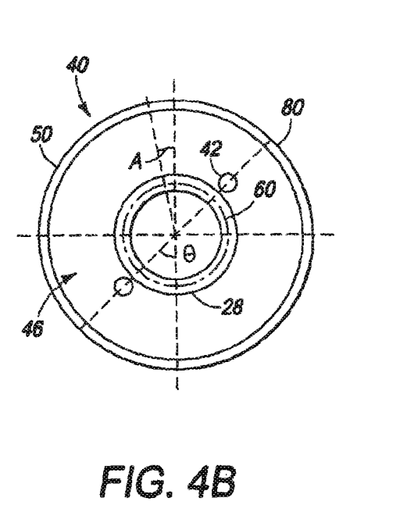
FIG. 4B is a front elevation view of the coupling interface at the distal end of the holder of the present combination instrument looking down the holder's axis to illustrate how it might be disposed to accept the tool head.
Figure 5:
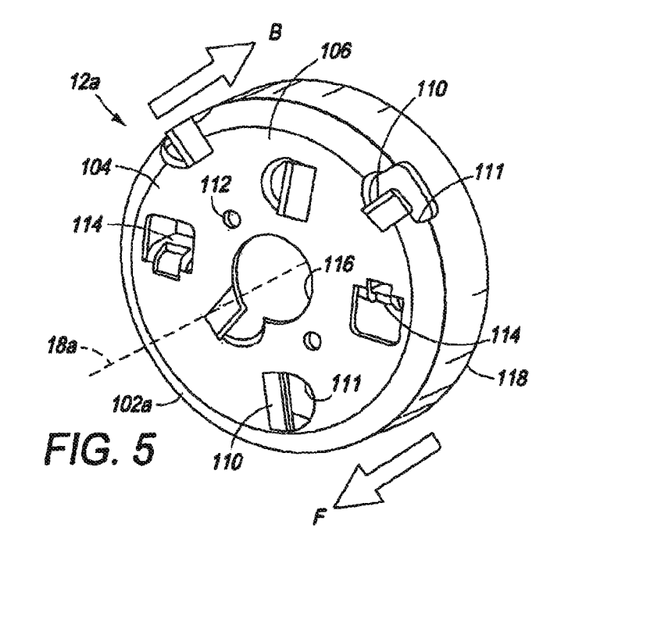
FIG. 5 is a perspective view of an alternative embodiment of a reamer/planer with a patella cutting tool head for use in the present combination instrument.

As shown in FIGS. 4A-4B and FIG. 5, a surgical tool 12 of the present invention is adapted to connect to a surgical tool holder 11. The tool 12 has a flat base portion 104, and has a front cutting/tool face 106, a back mounting face 108, an outer perimeter 102 and a central tool axis 18a. Cutting teeth 110, as are known in the field, project forward from the cutting face 106. The cutting teeth having a debris port 111, through which cutting debris is channeled to the space behind the flat base portion 104 of the tool 12. At least one, and preferably two or more complementary fitting interfaces 114, project backward from the back mounting face 108. In the embodiment illustrated, the complementary fitting interfaces 114 are tangs, and are adapted to be received by the fitting slots 84 on the coupling interface 40 of the surgical tool holder 11. Similar kinds of fitting interfaces 114 are selectable by one of skill in the art which can similarly be machine stamped or punched into the base 104 of a flat tool 12. All that is necessary is to have a feature engageable by the fitting slots 84. Pin detents 112, which in the embodiment illustrated are through apertures, are appropriately disposed to receive and hold the locking pins 42 of the tool holder 11, after the tool head 12, 12a is inserted in the coupling assembly 24 and rotated the appropriate angle A. This engages the tool 12, 12a with the tool holder 11 and, prevents the holder 11 from rotating relative to the tool 12, 12a, to hold the tool 12, 12a and handle 11 in an operable combination.

The surgical tool 12 further comprises an alignment bore 116 concentric with the tool axis 18a. When attached to the holder 11, the tool axis 18a and the shank axis 18 are coaxial. The alignment bore 116 is adapted to closely receive the collar bore 60 of guide portion 28 of the holder 11, and to be able to pivot thereabout. The alignment bore 116 provides an interface between the tool 12 and the holder's collar bore 60 to prevent radial displacement of the tool 12 relative to the holder 11 during use. In an alternative embodiment, the flat base portion 104 of the surgical tool 12a has a protective rim skirt 118 projecting backward from it. The rim skirt projects sufficiently backward from the outer perimeter 102a to facilitate manipulating the tool 12a at an in situ work site. Preferably, the surgical tools 12 and 12a of the present invention are adapted to be disposable. That is, that they are made from a material and/or by a manufacturing means that is inexpensive relative to the cost of having to clean and sterilize the tool. For example, note the tool 12 is simple in it geometric form and flat, machine stamped construction. Such forms, whether flat 12 or shallow cylinders 12a, are inexpensive to manufacture, therefore, supportive of single use. Also, this feature facilitates providing a clean and sterile combination orthopedic surgical instrument 10 after use.

Figure 3A:
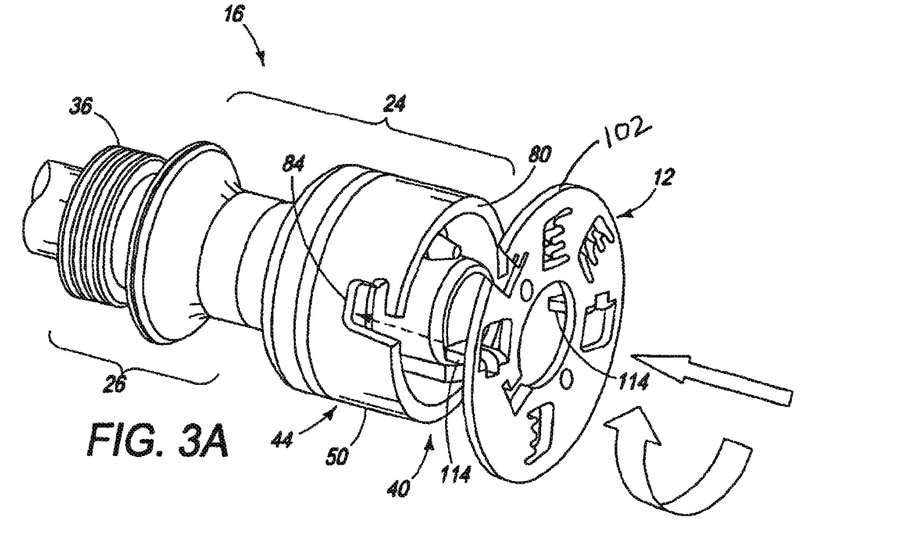
FIGS. 3A and 3B are perspective views of the shank coupling end of the combined instrument of the present invention in respective configurations: wherein the holder coupling is disengaged (unlocked) and the tool head positioned to be attached to the holder; and wherein the holder coupling is engaged with the tool head and the combined instrument is in an assembled configuration.
Figure 3B:
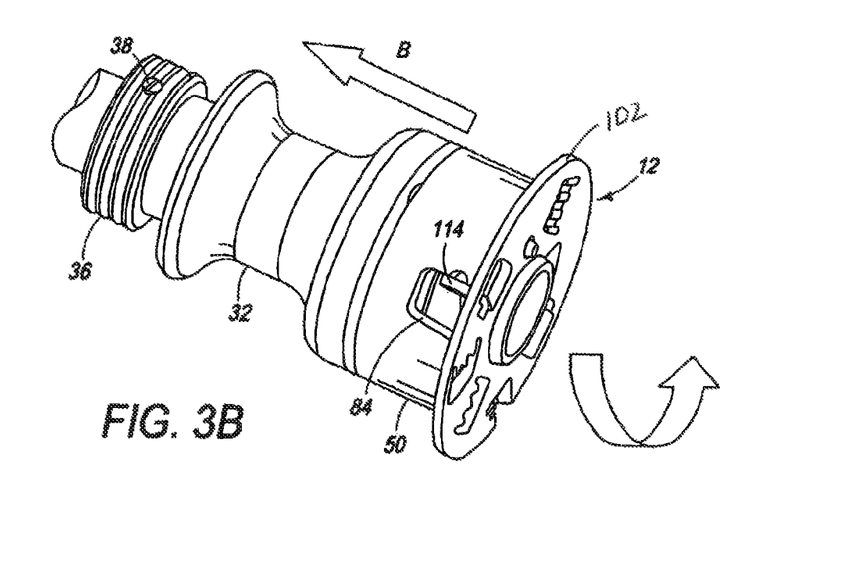

Referring to FIG. 3A, the holder 11 is shown ready to receive the tool 12. In use, the tool 12 is initially joined with the holder by inserting the tangs 114 into their respective fitting slots 84, and aligning the guide surface 60 with the alignment bore 116. Once aligned, the tool 12 is pressed backward against the pins 42 over the bias force thereon, until the back surface 108 of the tool interfaces with the rim 80 of the reservoir 44. Then the tool 12 and the holder 11 are rotated a small angle A (see FIG. 4B) until the pins 42 snap into their respective detents 112. Separation of the tool 12 from the holder 11 is as easily accomplished substantially by simply reversing this procedure. See FIG. 3B.

Figure 8:
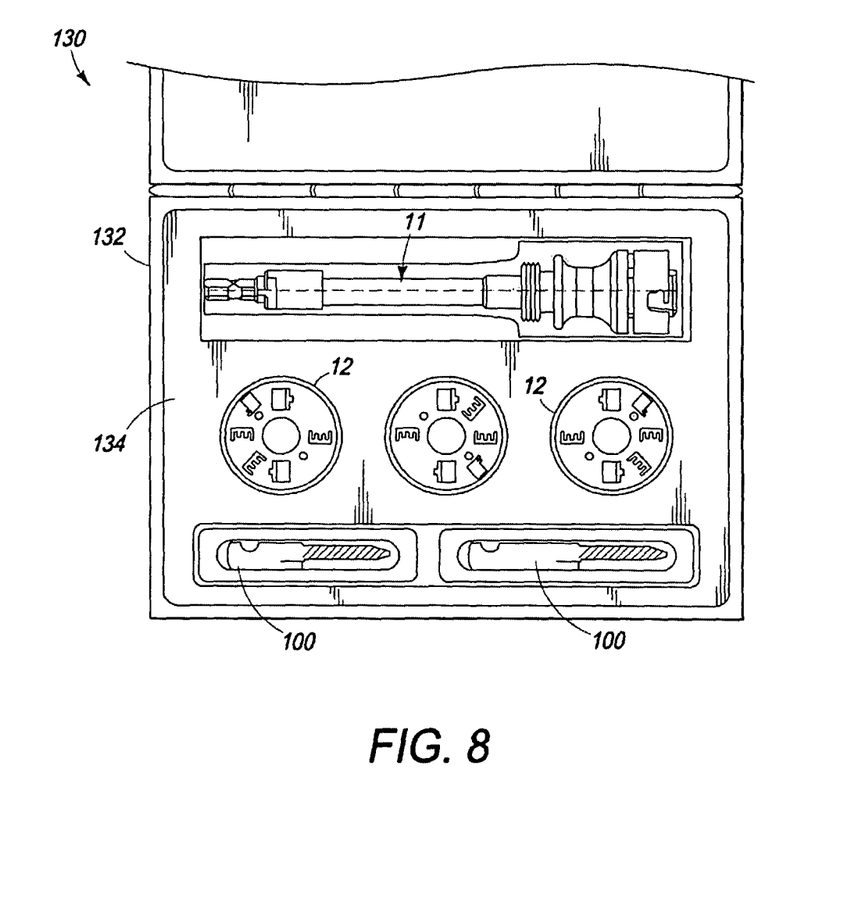
FIG. 8 is a kit for the present combination holder/tool head instrument, including the holder and a selection of tool heads.

Referring now to FIG. 8, collectively, these different components of the present invention can be a kit 130. The kit illustrated is a lidded container 132 with an internal compartmented separator/organizer 134. Further, the kit includes a selection of different tools 12 and 12a together with a tool holder 11. The kit 130 can also include different guides 100 and 101 specifically adapted for use with the present invention (see FIGS. 6 and 7).

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

What is claimed is:

1. A combination orthopedic surgical instrument, comprising:
   a) a surgical tool holder, comprising:
      i) a holder shank extending along a central axis from a coupling end to a drive end; and
      ii) a coupling assembly disposed on the coupling end of the holder shank, the coupling assembly having a reservoir comprising a side wall extending distally from a base to a forward rim,
      iii) wherein at least one fitting slot extends part way along a length of the reservoir side wall from the rim toward the base, the fitting slot comprising a narrower opening portion at the rim, the narrower opening portion being in open communication with a wider opening portion closer to the base to thereby form an extending portion of the side wall delineating the narrower opening portion from the wider opening portion;
   b) a tool, comprising:
      i) a base portion having a thickness extending from a forward cutting face to a back mounting face, wherein at least one detent extends from the back mounting face at least part way through the thickness of the base portion;
      ii) at least one cutting tooth projecting forwardly from the forward cutting face, the cutting tooth having a debris port for channeling cutting debris through the thickness of the base portion; and
      iii) at least one fitting portion projecting distally from the back mounting face, wherein a fitting opening resides where the fitting portion projects from the back mounting face; and
   c) a locking assembly, comprising:
      i) a collar slidably received on the shank;
      ii) a locking ring slidably received on the shank at a proximal location with respect to the collar;
      iii) a biasing member slidably received on the shank and biasing between a distal face of the locking ring and a proximal seat of the collar; and
      iv) at least one tool locking pin projecting from a forward face of the collar in a direction parallel to the central axis of the shank, each tool locking pin having a length that is sufficient to extend beyond the forward rim of the reservoir when the collar contacts the base of the reservoir,
   d) wherein with the back mounting face of the tool proximate the forward rim of the reservoir and with the fitting opening in the tool aligned with the extending portion of the side wall of the reservoir, the tool is rotationally manipulatable relative to the central axis of the holder shank to cause the extending portion of the reservoir side wall to move into the fitting opening of the tool to thereby detachably connect the tool to the tool holder, and
   e) wherein the collar is then manipulatable in a distal direction along the shank to contact the base of the reservoir with the at least one tool locking pin extending beyond the forward rim of the reservoir and received in the at least one detent of the base portion of the tool, and
   f) wherein the locking ring is then manipulatable in a distal direction along the shank to bias the biasing member against the proximal seat of the collar to bias the at least one tool locking pin, in the at least one detent and thereby prevent relative rotational movement of the tool with respect to the tool holder.

2. The combination orthopedic surgical instrument of claim 1, wherein the locking ring is engageable with the holder shank by a lock interface that when locked fixes the locking ring at a position on the shank relative to the coupling assembly to thereby lock the tool holder to the tool, and when unlocked allows the tool to be separated from the tool holder.

3. The combination orthopedic surgical instrument of claim 2, wherein the lock interface of the locking assembly is a set screw engaging the holder shank to fix the relative position of the locking ring on the shank.

4. The combination orthopedic surgical instrument of claim 2, wherein the lock interface of the locking assembly is a bayonet-type lock interface.

5. The combination orthopedic surgical instrument of claim 4, wherein the bayonet-type lock interface comprises:
   a) a tracking groove inset into a surface of the holder shank parallel to the shank axis, the tracking groove running from a first groove end to a second groove end toward the drive end of the shank;
   b) a release slot disposed proximate the first groove end of the tracking groove, the release slot having an "L/J-like" configuration and communicating with the tracking groove; and
   c) a guide pin slidably receivable in the release slot and tracking groove, the guide pin radially projecting from an inner ring surface of the locking ring; and
   d) the locking ring being manually operable to move the guide pin along the tracking groove and reversibly settable into the release slot against a bias force of the biasing member, the bias force serving to lock the guide pin in the release slot and to lock the biasing member against the proximal seat of the collar to thereby lock the at least one tool locking pin in the at least one detent and prevent relative rotational movement, of the tool with respect to the tool holder.

6. The combination orthopedic surgical instrument of claim 1, wherein the drive end of the holder shank further comprises a drive adaptor connectable to a manipulator, the drive end having a stop shoulder having a stop diameter (Ds) that is larger than an inner ring diameter (Dr) of the locking ring to thereby prevent the locking ring from sliding off of the shank.

7. The combination orthopedic surgical instrument of claim 1, wherein the drive end of the holder shank further comprises a drive adaptor for interfacing the tool holder with a manipulator, the drive adaptor being selected from the group consisting of: a male hex interface, a female hex interface, a bayonet-type interface, and an AO fitting interface.

8. The combination orthopedic surgical instrument of claim 1, wherein the coupling end of the holder shank further comprises a guide portion having an internal guide recess set into the shank, the guide recess being coaxial with the central axis of the shank, and adapted to receive a guide pin.

9. The combination orthopedic surgical instrument of claim 8, wherein the internal guide recess set into the coupling end of the holder shank is cylindrical and has an internal surface serving as a bushing within which the guide pin may slide and rotate.

10. The combination orthopedic surgical instrument of claim 8, wherein the holder shank further comprises a cannula within the holder shank running internally along the central axis of the holder shank and being in flow communication with the guide recess, the cannula being useful for lavage and providing a channel for removing cutting debris from the reservoir of the tool holder.

11. The combination orthopedic surgical instrument of claim 1, wherein the at least one tool locking pin passes through a pin guide hole in the base of the reservoir.

12. The combination orthopedic surgical instrument of claim 1, wherein the biasing member is a helical compression spring.

13. The combination orthopedic surgical instrument of claim 1, wherein the base portion of the tool has a protective rim skirt.

14. The combination orthopedic surgical instrument of claim 1, wherein the tool is adapted to be disposable.

15. A kit, comprising:
   a) a lidded container with shaped compartments;
   b) the combination, orthopedic surgical instrument of claim 1, wherein the tool holder and at least one tool are received in at least one of the shaped compartments; and
   c) an instruction set relating to assembly or care of the combination orthopedic surgical instrument.

16. The combination orthopedic surgical instrument of claim 1, wherein the at least one fitting slot comprises two opposed fitting slots forming respective extending portions of the side wall, and wherein the at least one fitting opening comprises two opposed fitting openings, wherein the extending portions of the side wall are receivable in the fitting openings.

17. A combination orthopedic surgical instrument, comprising:
   a) a surgical tool holder, comprising:
      i) a holder shank extending along a central axis from a coupling end to a drive end; and
      ii) a coupling assembly disposed on the coupling end of the holder shank, the coupling assembly having a reservoir comprising a side wall extending distally from a base to a forward rim,
      iii) wherein at least one fitting slot extends part way along a length of the reservoir side wall from the rim toward the base, the fitting slot comprising a narrower opening portion at the rim, the narrower opening portion being in open communication with a wider opening portion closer to the base to thereby form an extending portion of the side wall delineating the narrower opening portion from the wider opening portion;
   b) a tool, comprising:
      i) a base portion having a thickness extending from a forward cutting face to a back planar mounting face, wherein at least one detent extends from the back planar mounting face at least part way through the thickness of the base portion;
      ii) at least one cutting tooth projecting forwardly from the forward cutting face, the cutting tooth having a debris port for channeling cutting debris through the thickness of the base portion; and
      iii) at least one second planar fitting portion projecting distally from the back planar mounting face, wherein a fitting opening resides where the second planar fitting portion projects from the back planar mounting face; and
   c) a locking assembly, comprising:
      i) a collar slidably received on the shank;
      ii) a locking ring slidably received on the shank at a proximal location with respect to the collar;
      iii) a biasing member slidably received on the shank and biasing between a distal face of the locking ring and a proximal seat of the collar; and
      iv) at least one tool locking pin projecting from a forward face of the collar in a direction parallel to the central axis of the shank, each tool locking pin having a length that is sufficient to extend beyond the forward rim of the reservoir when the collar contacts the base of the reservoir,
   d) wherein with the back planar mounting face of the tool proximate the forward rim of the reservoir and with the fitting opening in the tool aligned with the extending portion of the side wall of the reservoir, the tool is rotationally manipulatable relative to the central axis of the holder shank to cause the extending portion of the reservoir side wall to move into the fitting opening where the second planar fitting portion projects from the back planar mounting face of the tool to thereby detachably connect the tool to the tool holder, and e) wherein the collar is then manipulatable in a distal direction along the shank to contact the base of the reservoir with the at least one tool locking pin extending beyond the forward rim of the reservoir and received in the at least one detent of the base portion of the tool, and f) wherein the locking ring is then manipulatable in a distal direction along the shank to bias the biasing member against the proximal seat of the collar to bias the tool locking pin in the detent and thereby prevent relative rotational movement of the tool with respect to the tool holder.

18. A surgical tool holder assembly, comprising:
a) a surgical tool holder, comprising:
   i) a holder shank extending along a central axis from a coupling end to a drive end; and
   ii) a coupling assembly disposed on the coupling end of the holder shank, the coupling assembly having a reservoir comprising a side wall extending distally from a base to a forward rim,
   iii) wherein at least one fitting slot extends part way along a length of the reservoir side wall from the rim toward the base, the fitting slot comprising a narrower opening portion at the rim, the narrower opening portion being in open communication with a wider opening portion closer to the base to thereby form an extending portion of the side wall delineating the narrower opening portion from the wider opening portion; and
b) a locking assembly, comprising:
   i) a collar slidably received on the shank;
   ii) a locking ring slidably received on the shank at a proximal location with respect to the collar;
   iii) a biasing member slidably received on the shank and biasing between a distal face of the locking ring and a proximal seat of the collar; and
   iv) at least one tool locking pin projecting from a forward face of the collar in a direction parallel to the central axis of the shank, each tool locking pin having a length that is sufficient to extend beyond the forward rim of the reservoir when the collar contacts the base of the reservoir,
c) wherein the collar is manipulatable in a distal direction along the shank to contact the base of the reservoir with each tool locking pin extending beyond the forward rim of the reservoir, and
f) wherein the locking ring is then manipulatable in a distal direction along the shank to bias the biasing member against the proximal seat of the collar to thereby bias each tool locking pin extending beyond the forward rim of the reservoir.

19. The surgical tool holder assembly of claim 18, wherein the locking ring is engageable with the holder shank by a lock interface that when locked fixes the locking ring at a position on the shank relative to the coupling assembly.

20. The surgical tool holder assembly of claim 19, wherein the lock interface of the locking assembly is a set screw engaging the holder shank to fix the relative position of the locking ring on the shank.

21. The surgical tool holder assembly of claim 19, wherein the lock interface of the locking assembly is a bayonet-type lock interface.

22. The surgical tool holder assembly of claim 21, wherein the bayonet-type lock interface comprises:
a) a tracking groove inset into a surface of the holder shank parallel to the holder shank central axis, the tracking groove running from a first groove end to a second groove end toward the drive end of the shank;
b) a release slot disposed proximate the first groove end of the tracking groove, the release slot having an "L/J-like" configuration and communicating with the tracking groove; and
c) a guide pin slidably receivable in the release slot and tracking groove, the guide pin radially projecting from an inner ring surface of the locking ring; and
d) the locking ring being manually operable to move the guide pin along the tracking groove and reversibly settable into the release slot against a bias force of the biasing member, the bias force serving to lock the guide pin in the release slot and to lock the biasing member against the proximal seat of the collar.

23. The surgical tool holder assembly of claim 18, wherein the drive end of the holder shank further comprises a drive adaptor connectable to a manipulator, the drive end having a stop shoulder having a stop diameter (Ds) that is larger than an inner ring diameter (Dr) of the locking ring to thereby prevent the locking ring from sliding off of the shank.

24. The surgical tool holder assembly of claim 18, wherein the drive end of the holder shank further comprises a drive adaptor for interfacing the tool holder with a manipulator, the drive adaptor being selected from the group consisting of: a male hex interface, a female hex interface, a bayonet-type interface, and an AO fitting interface.

25. The surgical tool holder assembly of claim 18, wherein the coupling end of the holder shank further comprises a guide portion having an internal guide recess set into the shank, the guide recess being coaxial with the central axis of the shank, and adapted to receive a guide pin.

26. The surgical tool holder assembly of claim 25, wherein the internal guide recess set into the coupling end of the holder shank is cylindrical and has an internal surface serving as a bushing within which the guide pin may slide and rotate.

27. The surgical tool holder assembly of claim 18, wherein the holder shank further comprises a cannula within the holder shank running internally along the central axis of the holder shank and being in flow communication with a guide recess, the cannula being useful for lavage.

28. The surgical tool holder assembly of claim 18, wherein the biasing member is a helical compression spring.

* * * * *